United States Patent [19]
Pazda et al.

[11] Patent Number: 4,862,065
[45] Date of Patent: Aug. 29, 1989

[54] ON-LINE WEB INTERNAL RESISTIVITY MEASURING APPARATUS

[75] Inventors: Robert J. Pazda, Waterloo; Kenneth L. Clum, Webster, both of N.Y.

[73] Assignee: Eastman Kodak Company, Rochester, N.Y.

[21] Appl. No.: 178,700

[22] Filed: Apr. 7, 1988

[51] Int. Cl.$^4$ ................ G01R 27/02; G01R 27/26
[52] U.S. Cl. ................ 324/65 R; 324/65 P; 324/558
[58] Field of Search ............. 73/159; 324/65 R, 65 P, 324/61 P, 61 R, 558

[56] References Cited

U.S. PATENT DOCUMENTS

| | | | |
|---|---|---|---|
| 2,870,405 | 1/1959 | Wright | 324/65 R |
| 3,916,789 | 11/1975 | Watts | 324/61 P |
| 4,546,310 | 10/1985 | Chatanier | 324/65 R |
| 4,674,325 | 6/1987 | Kiyobe | 73/159 |

Primary Examiner—Reinhard J. Eisenzopf
Assistant Examiner—Jose M. Solis
Attorney, Agent, or Firm—Edward Dugas

[57] ABSTRACT

A web roller is provided with at least two electrodes that are positioned parallel to each other on the roller surface end parallel to the longitudinal axis of the roller. Slip rings provide individual electrical connections to the electrodes. The electrodes are spaced apart a distance which permits both electrodes to be in contact with a web of sheet material of the type having a conductive center sandwiched between layers of insulating sheet. A position detector, positioned to detect the rotation of the roller, provides a pulse signal of a known magnitude to one of the electrodes, through a slip ring, when the electrodes are in contact with the web of sheet material. A sensor coupled to the other electrode, through a slip ring, receives the pulse signal after it has passed through the sheet material located between the two electrodes. The magnitude of the received pulse is a function of the resistivity of the sheet material.

6 Claims, 4 Drawing Sheets

ON-LINE WEB INTERNAL RESISTIVITY MEASURING APPARATUS

BACKGROUND OF THE INVENTION

The present invention is directed to an apparatus for continuously measuring the internal resistivity of a web of sheet material as the material is moved over a roller.

It is desirable to accurately measure the internal resistivity of a conducting layer sandwiched between insulating layers of sheet material while the sheet is moving through a machine at a relatively high speed.

With the internal resistivity known, it can be determined in advance whether a given sheet product, such as a photographic paper, will encounter electrostatic problems during sensitizing, finishing, or customer operations. Paper stock resistivity influences important electrostatic effects associated with moving webs and, therefore, maintaining internal resistivity within a limited range can prevent many electrostatic problems. For example, a low resistivity paper stock prevents the build up of a net charge on the surface of a moving web. If the charge did build up, the resulting electric fields could cause an air breakdown creating a spark or corona, which in turn would expose the emulsion layer on the photographic paper. In addition, low resistivity paper stock provides a means of preventing winding rolls from obtaining a high electrical potential which can result in external fields that can be hazardous not only to the product, but also to personnel. If the paper stock resistivity is too low, however, it can cause problems when the moving web is treated with high voltage sources, such as is used in a Corona Discharge Treatment (CDT). Excessive currents will propagate along the conducting moving web and can again be hazardous to personnel and product. In the case of extremely high paper resistivity, devices used to treat the web surface, may become ineffective.

Instrumentation is currently available for measuring the internal resistivity of a resin-coated sheet, but the measurement is accomplished off-line and is done normally several hours after the sample has been taken. During this time it is possible for the internal resistivity to change due to humidity conditions which, therefore, can lead to misleading results. In addition, if the internal resistivity is found to be either too high or too low, nothing can be done to correct the situation because the stock roll has already been sensitized.

A prior art patent of interest for its teaching of measuring resistivity in a moving web material is U.S. Pat. No. 2,870,405 entitled "Apparatus For Measuring Moisture in Web Coatings" by R. A. Wright et al. The aforementioned patent is assigned to Eastman Kodak Co., the assignee of the present application. The apparatus of that patent utilizes a roller having a plurality of radially projecting ribs extending parallel to the roller's long axis. Alternate ones of the ribs are electrically connected to ground through a slip ring and a measurement device, such as an ampmeter. Every other one of the ribs is connected to a d.c. source through a second slip ring. The circuit path from the d.c. source to ground is completed by the web material. The current flow through the resultant circuit is a function of the resistivity of the web material. Such an apparatus is sufficient for having a surface that is measuring webs of material if the whole web is conductive, but for materials which have the conductive layer sandwiched between layers of electrically insulating material, the apparatus will not work.

Another patent of interest is U.S. Pat. No. 2,942,243 entitled "Apparatus and Method For Detecting Abrupt Changes in Dielectric Sheet Material" by W. H. Huggins. In the apparatus of that patent, a sheet of dielectric material is passed between two electrodes with one of the electrodes being formed from a plurality of skids which yieldably engage the dielectric material. The apparatus functions not to measure resistance but to detect bumps, creases or other sudden changes in the thickness of the dielectric sheet material by creating a voltage pulse which is a.c. coupled to amplifiers that drive some form of alarm or indicating device.

Because the patented apparatus uses electrodes which make sliding contact with the surface of the material being monitored, the apparatus cannot be used to monitor webs of materials having a sensitized outer layer because the skids will physically harm the sensitized layer. In addition, the patented apparatus will not respond to slow changes in material thickness because it generates a voltage pulse by a quick, or transient change, in the spacing between the two electrodes.

SUMMARY OF THE INVENTION

The apparatus of the present invention utilizes an insulating roller with two closely spaced electrodes positioned on the outer surface of the roller extending parallel to the roller's long axis. Slip-rings provide individual electrical connections between the electrodes and external instrumentation. A position detector, which may be a photodetector, provides a signal which indicates when both electrodes are in contact with a web material that is passed over the roller. A pulse generator provides a voltage pulse through a slip-ring to the one electrode. A sensor, including an amplifier, is connected through a slip-ring to the other electrode to detect the resulting pulse at the second electrode. The magnitude of the received pulse is a function of the resistivity of the internal paper forming the web.

The present apparatus uses low voltage pulses, on the order of 5V, which causes no damage to the sensitized web material and which are safe for persons who operate the apparatus and who handle the web after the monitoring process.

From the foregoing it can be seen that it is a primary object of the present invention to provide a measuring apparatus for use with a web of conducting material sandwiched between layers of insulating material.

It is another object of the present invention to provide a resistivity measuring apparatus which uses a low electrical potential.

It is a further object of the present invention to provide an apparatus which can measure the resistivity of a web material as the material is moved at high speed over the apparatus.

These and other objects of the present invention will become more apparent from the following description and drawings, which drawings form a part of the specification and wherein like characters indicate like parts.

DESCRIPTION OF THE PREFERRED EMBODIMENT

Figure 1:
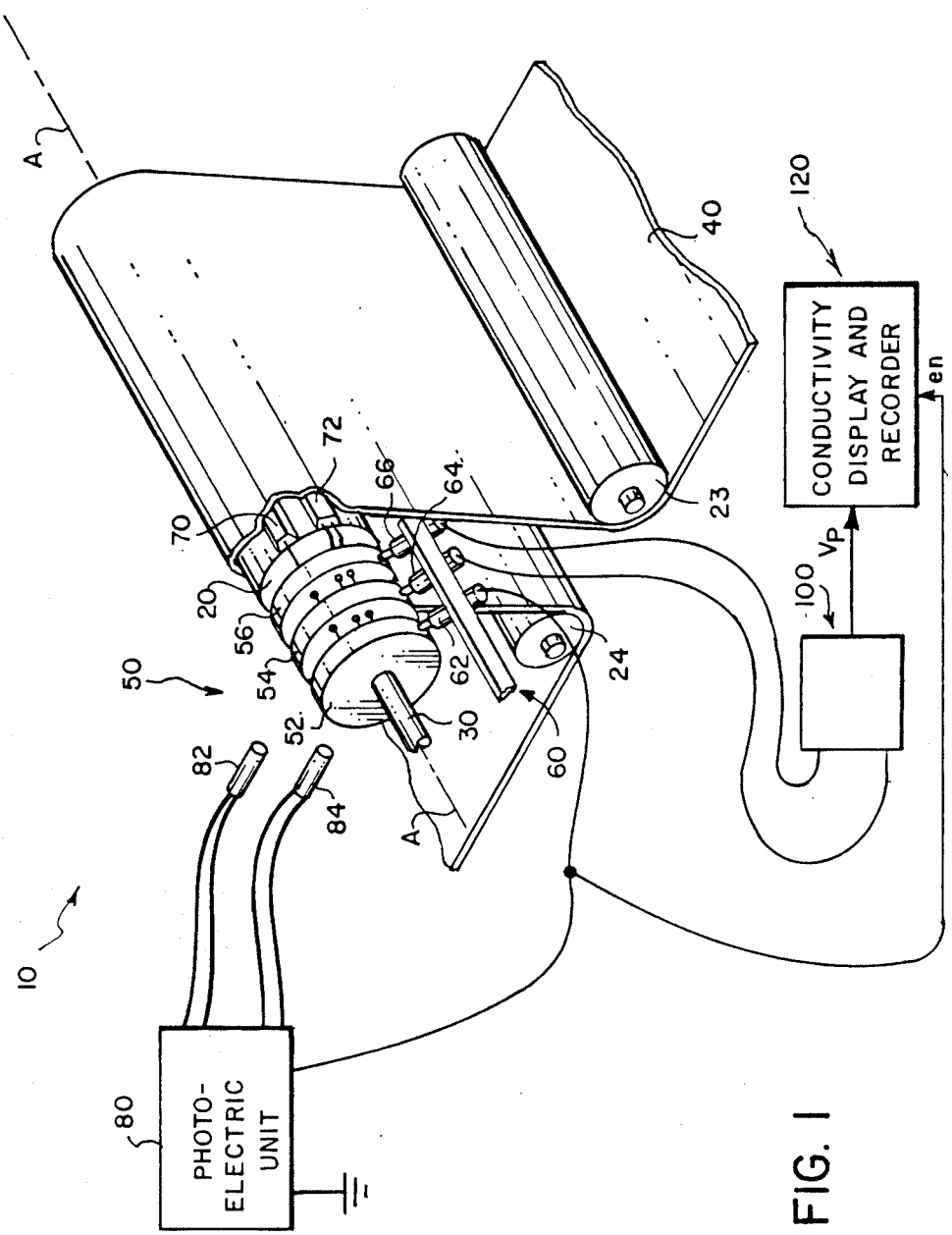
FIG. 1 is a view partially in perspective and partially diagrammatic showing an apparatus constructed in accordance with the present invention.

Referring to FIG. 1, the apparatus 10 is shown engaging a sheet of web material 40 over rollers 20, 23 and 24. In the preferred embodiment of the invention, it is desirable to have the web material engage the surface of the roller 20 for approximately 180 degrees of contact. The reason for this, although not a requirement, will be described later in this description of the invention. The roller 20 is designed to rotate on a shaft 30 around a long axis defined by the line A—A. Positioned on the surface of the roller 20, parallel to the long axis and spaced apart from each other, are a first electrode 70 and a second electrode assembly 72. These electrodes are insulated from the surface of the roller 20 and from each other. Electrical connection to and from the electrodes is via a set of slip-rings 50 which are operatively coupled to a brush set 60. In the preferred embodiment, three slip-rings 52, 54 and 56 are used, with signals passing between the slip rings and the external instruments via brushes 62, 64 and 66, respectively. A photoelectric unit 80 powers a lamp 84 to project a beam of light onto the rotating shaft 30 of the roller 20. The beam of light illuminates an index mark 86 (shown in FIG. 3) on the shaft 30. The index mark is positioned such that when the electrodes 70 and 72 are in contact with the web material 40, a photo detector 82 senses the index mark and provides an input signal to the photoelectric unit 80. The photoelectric unit 80 then provides an output pulse to the electrode 70 via the brush and slip-ring assembly 62 and 52, respectively. The output of the photoelectric unit 80 is also used to enable conductivity display and recorder 120 which has its inputs connected to the electrode assembly 72 via the brush and slip-ring assembly, specifically slip-rings 54 and 56 and brushes 64 and 66. The pulse detector 100 detects the occurrence of a pulse being received at the electrode assembly 72 after being generated by the pulse generator 80 and traversing the web material 40 between the electrode 70 and the electrode assembly 72. The output of the pulse detector is a voltage $V_p$. The output voltage $V_p$ from the pulse detector 100 may be directed to a conductivity display and recorder 120 for indicating either to an operator and/or to a control computer the resistivity of the web material 40.

Each revolution of the roller 20 corresponds to a like movement of the web material such that in operation the web material is tested for resistivity along its entire length at locations spaced apart a distance equivalent to the circumference of the roller 20.

Figure 2:
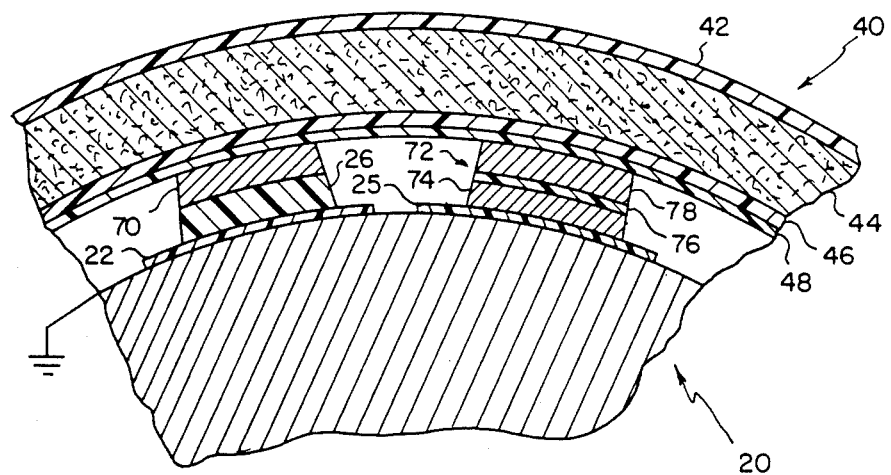
FIG. 2 is an enlarged sectional view of a segment of the roller used in the apparatus of FIG. 1 illustrating the positioning of the web material on the electrodes and the mounting of the electrodes to the roller surface.

Referring now to FIG. 2 which is an enlarged and sectional view illustrating the segment of the roller containing the electrodes 70 and 72 along with a segment of the web material that is to be tested with the present apparatus. The roller 20 is provided with at least two spaced apart insulators 22 and 25 on its outer surface. A second insulator 26 is positioned over insulator 22 to increase the material thickness in this area. The voltage electrode 70 is affixed to insulator 26. The voltage electrode 70 is shown exaggerated in thickness for purpose of explanation but, in fact, is only one mil thick (0.001 inch). Spaced apart from the voltage electrode 70 is the electrode assembly 72 which is comprised of a guard electrode 74 that is one mil thick, affixed to the insulator 25, a sense electrode 78 which is one mil thick, and an insulating layer 76 which separates the two electrodes. The distance between the electrode 70 and the electrode assembly 72, in the preferred embodiment of the present invention, was two millimeters. The roller 20 is conductive in nature and is connected to a ground potential. In the preferred embodiment of the invention the roller 20 was 4 inches in diameter by 54 inches in length.

The web of material 40 is comprised of a paper center section 44 sandwiched between insulating resin coating layers 42 and 46. The paper layer 44 has a resistivity which is to be measured between the electrodes 70 and 72. Additionally, on one surface of the web material 40 there may be deposited an anti-stat layer 48. The anti-stat layer 48 and the resin coat layer 46 separate the paper layer 44 from direct electrical contact with the electrodes 70 and 72. Again, in FIG. 2 the height of the electrodes along with their width is greatly exaggerated, and the web material, when it rolls into contact with the electrodes is not deformed from the surface of the roller by any significant amount.

Although the preferred embodiment of the invention has electrodes projecting from the surface of the roller 20 it would be obvious, in view of Applicants' teaching that the electrodes could be recessed flush with the outer surface of the roller, and also that multiple sets of electrodes could be positioned on the roller to provide multiple measurement for each roller rotation.

Figure 3:
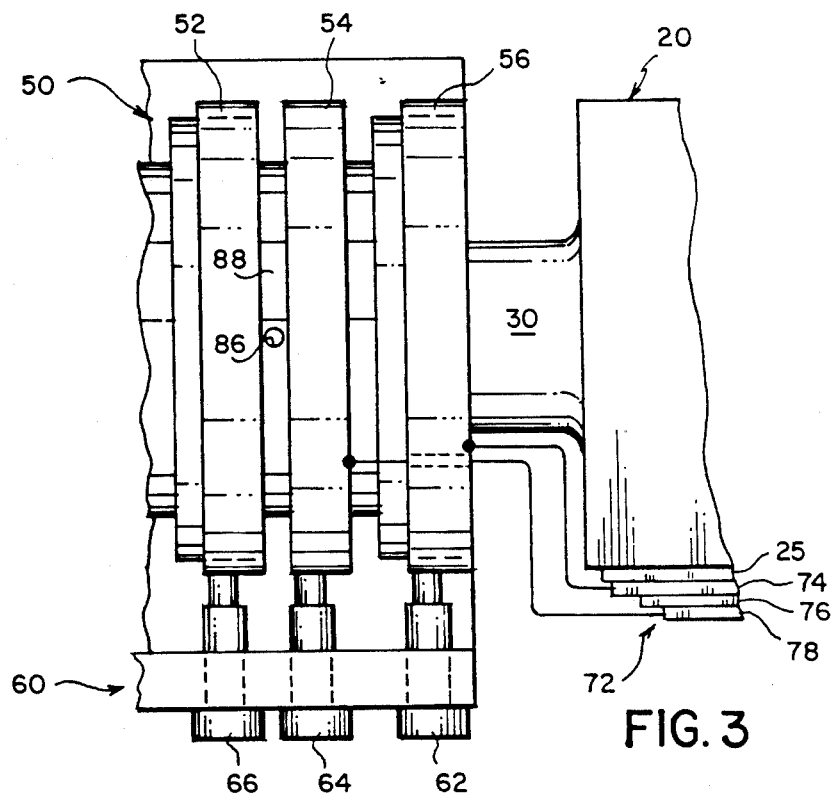
FIG. 3 is an enlarged cut away view of a portion of the roller illustrating a slip-ring assembly.

Referring now to FIG. 3 wherein the slip-ring arrangement 50 along with the brush assembly 60 is shown in detail. Projecting from one end of the roller 20 is a shaft 30 onto which is mounted a slip-ring assembly 50. The slip-ring assembly is comprised of three conductive slip-rings 52, 54 and 56 which are rigidly fixed to the shaft 30 but which are electrically insulated therefrom by means well known in the art. The brush assembly 60 is affixed to the apparatus in a stationary position adjacent the slip-rings 50. The brush assembly 60 rigidly positions a set of carbon brushes 62, 64 and 66 into electrical contact with the slip-rings 52, 54 and 56, respectively. The electrode assembly 72 has the electrode 78 connected to the slip-ring 54 with the elctrode 74 connected to the slip-ring 56. As previously described, the electrodes 74 and 78 are insulated from each other and from the surface of the roller 20 by insulating layer 76 and insulating layer 22. The third slip-ring 52 is connected to the electrode 70 in a manner identical to the connection of electrodes 74 and 78. Affixed to the shaft 30, intermediate to the slip-rings 54 and 56, is a ring of highly reflective material 88 onto which is affixed a spot of non-reflecting material 86. The non-reflecting material 86 provides the index for the photoelectric unit 80 to indicate the positioning of the electrodes in contact with the web material 40.

Figure 4:
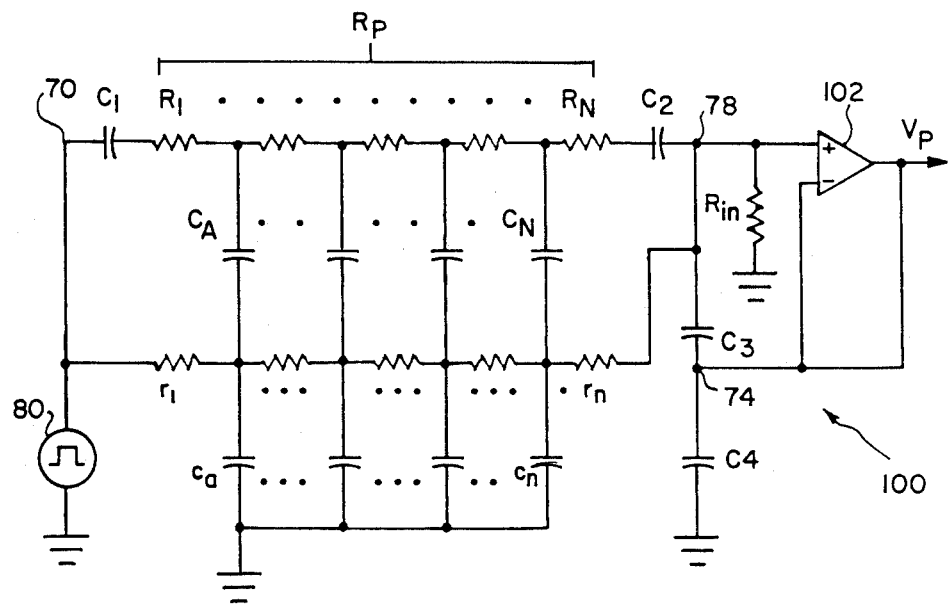
FIG. 4 is an electrical diagram illustrating a circuit which is electrically equivalent to the web being measured, in contact with the electrodes, shown connected to the electrical apparatus of FIG. 1.

Referring to FIG. 4 wherein the equivalent electrical circuit of the web material 40 is shown connected to the electrical apparatus of FIG. 1, the capacitor $C_1$ represents the capacitance between the electrode 70 and the paper 44. The capacitor $C_2$ represents the capacitance between the paper 44 and the electrode 78. $R_1 \ldots R_N$, in a series arrangement, represents the internal paper resistance ($R_p$) between the electrodes and is shown in equation 1. There exists a distributed capacitance along the paper resistance which is represented by $C_A \ldots C_N$. This is due to the resin coat 46 which lies across both electrodes and is between the internal paper resistance and the surface resistance ($r_s$) associated with the anti-stat layer 48, if present. There also exists a distributed air gap capacitance between the anti-stat layer surface and the grounded roller 20 which is represented by $c_a \ldots c_n$. The internal paper resistance and the surface resistance are two distinct characteristics and as such they are treated separately. The surface resistance between electrodes 70 and 78 is given by equation 2.

$$R_P = R_1 + R_2 + \ldots + R_N \tag{1}$$

$$r_s = r_1 + r_2 + \ldots + r_n \tag{2}$$

the third electrode 74 is used as a guard electrode to reduce or eliminate the capacitance between the sensor electrode 72 and the grounded roller 20. The low level d.c. pulse signal is sent to the electrode 70 as previously described produces a transient signal at the electrode 78 lasting anywhere between one millisecond and tens of milliseconds depending upon the value of $R_p$. To achieve a reduction in effective capacitance, from electrode 78 to ground a voltage follower circuit incorporating an operational amplifier 102 is used to feed back the signal to the guard electrode 74 in a procedure well known in the art.

The uniqueness of this measurement is that, with the web of material 40 being wrapped around the roller for approximately 180 degrees, the measurement is not made until the electrodes have been in contact with the web of material for approximately 90 degrees of the roller circumference. This gives any extraneous transient signals time to pass, not allowing them to interfere and cause erroneous results.

The timing pulse, provided by the photoelectric unit 80 serves two different functions. First it is used as the pulse signal sent to the electrode 70, and secondly it is used to enable the electronics 100 to capture and hold the transient response occurring at the sensor electrode 78.

The peak voltage ($V_P$) of the transient response is a function of the internal paper resistance, surface antistat resistance, and $C_1, C_2, C_A \ldots C_N$, and $c_a \ldots c_n$.

$R_P$ is the main parameter of interest and is the dominant factor in the peak transient voltage. $R_{in}$ is the resistance to ground at the positive input to the operational amplifier 102 and also has a strong influence on $V_P$. The surface resistance does not affect the voltage initially because it is normally one to two orders of magnitude higher in resistivity. Therefore, when a d.c. pulse is first applied to the apparatus, all of the current flow is through the paper until capacitors $C_1$ and $C_2$ charge. Then current flows through the surface resistance.

Figure 5:
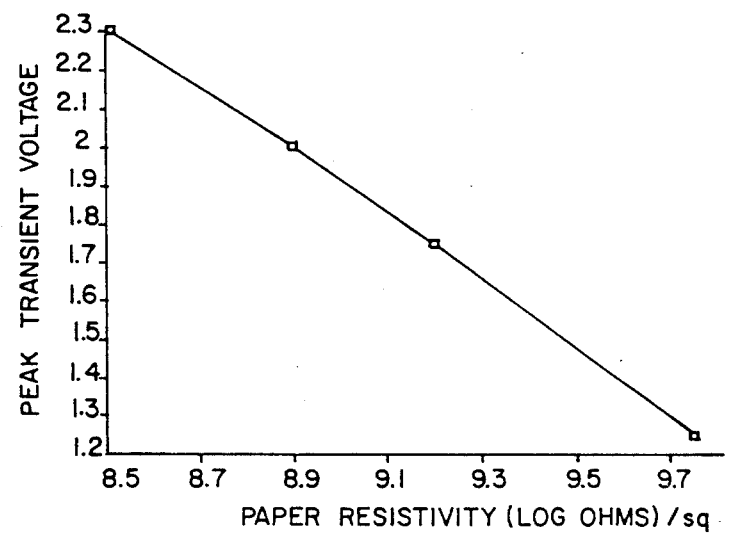
FIG. 5 is a graph illustrating the relationship between the peak voltage received by the electrical apparatus of FIG. 1, and the resistivity of the paper web.

Referring to the graph of FIG. 5, the graph is of the peak transient voltage versus paper resistivity in log ohms/sq. The unit "Log ohms/sq" is simply the common logarithm (base 10) of the resistivity ($R_P$). Units of log ohms/sq are commonly used, since the resistivity value is very large. This is the output from the detection circuitry connected to electrodes 78 and 74 when a 5-volt square pulse is applied to the electrode 70 The paper thickness was 9 mils (0.009 inches) and was resin-coated on both sides. Knowing the peak transient voltage, one can then calculate the corresponding paper resistivity. By extrapolating the graph at both ends, one can see that there is the capability of measuring the internal resistivity over at least two decades. The internal paper resistivity (P) in ohms/sq is related to the internal paper resistance $R_P$ as shown in equation 4, where w equals the width of the paper across the electrodes and d equals the separation between the electrodes. The constant w/d is referred to as the electrode factor. The units of P are ohms per square.

$$P = R_P \times (w/d). \tag{4}$$

P can vary over four decades ranging from seven log ohms/sq to eleven log ohms/sq depending on the paper stock. The internal resistivity can also vary considerably throughout a single stock roll in the width or length direction. Therefore, one could see a variation in internal resistivity with one roller revolution (equal to the distance of the circumference of a roller). The measurement presented here is actually an average of the internal resistivity in the width direction of a moving web and is updated every roller revolution.

Figure 6:
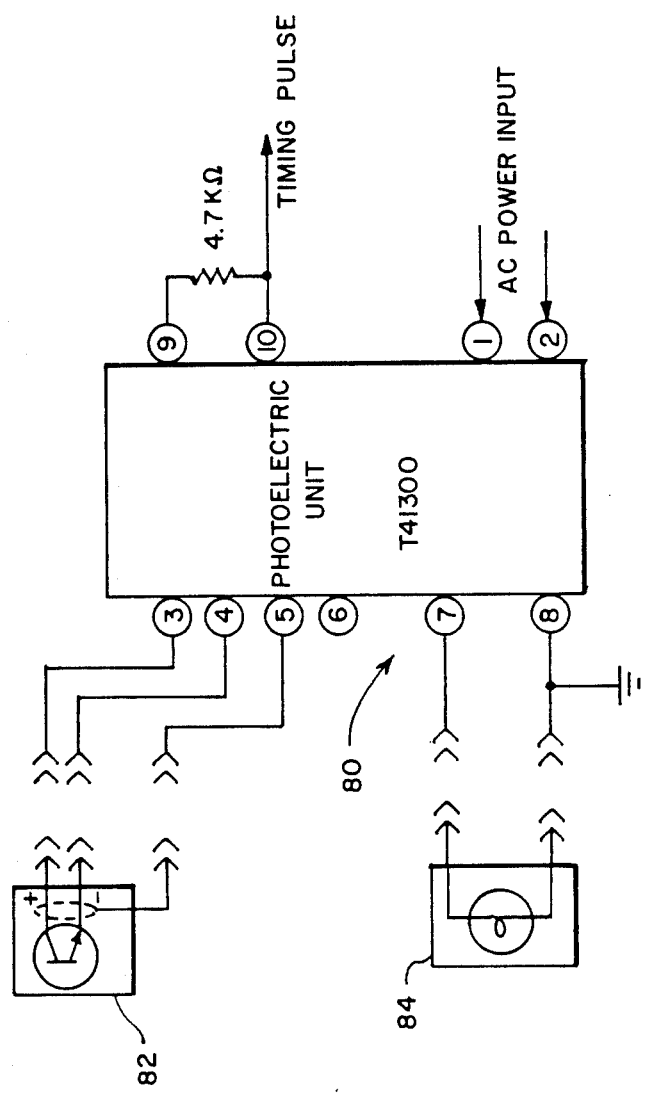
FIG. 6 is a block circuit diagram of a photoelectric unit which may be utilized with the apparatus of FIG. 1.

Referring now to FIG. 6 wherein is disclosed, the block circuit diagram of the photoelectric unit 80 coupled to a photo diode 82 and to an illuminating lamp 84. The photoelectric unit may be of the type that is commercially available from Skan-A-matic Corporation bearing their Part No. T41300. Such a photoelectric unit is powered by an a.c. power source at the inputs labeled 1 and 2 and upon receipt of a change in illumination by the photo diode 82 outputs a timing pulse signal on the terminal labeled 10. This signal is approximately 5 volts in magnitude and is directed to the electrode 70 for transmission through the paper web to the electrode assembly 72.

Although a specific embodiment of the invention has been shown in detail for purposes of disclosing the best mode of the invention, it will be apparent to those persons skilled in the art that various modifications may be made to the disclosed apparatus without departing from the spirit and scope of the invention. It is, therefore, intended that the invention be limited only by the terms of the appended claims.

We claim:

1. An apparatus for measuring the resistivity of a web of material comprised of a conductive sheet material sandwiched between layers of insulating material comprising:
   a roller having an outer surface and mounted for rotation about a longitudinal axis;
   a first insulator affixed to the outer surface of said roller;
   a first electrode affixed to said first insulator;
   a second insulator affixed to the outer surface of said roller;
   an electrode assembly comprising, a second electrode affixed to said second insulator parallel to said first electrode, an insulating layer affixed to said second electrode, and a third electrode affixed to said insulating layer;
   a source of pulses electrically coupled to said first electrode for providing pulses to said first electrode when the web is in contact with said first and said third electrode; and means electrically connected to said second and said third electrode for receiving the pulses passing from said first electrode through said web to provide a signal indicative of the resistivity of the conductive sheet material.

2. The apparatus according to claim 1 and further comprising:
means for maintaining the web of material in contact with said roller for approximately 180°; and
means for controlling said source of pulses to provide pulses to said first electrode after said web has been in contact with said first and said third electrode for approximately 90°.

3. An apparatus for measuring the resistivity of a moving sheet of layered material, said layered material formed from a conductive sheet sandwiched between layers of insulating material comprising:
a roller means having electrodes thereon for contacting said moving sheet wherein one of said electrodes is an assembly comprised of:
an insulating layer affixed to said roller;
a guard electrode affixed to said insulating layer;
an insulating layer affixed to said guard electrode;
a signal electrode affixed to said insulating layer;
pulse means for generating a voltage pulse;
amplifying means for receiving and amplifying voltage pulses said amplifying means having two inputs one electrically connected to said guard electrode and the amplifying means output and the other connected to said signal electrode; and
means for electrically connecting said pulse means and said amplifying means to said electrodes on said roller means such that the amplitude of a received pulse is a function of the conductivity of said conductive sheet.

4. The apparatus according to claim 3 wherein said means for electrically connecting is comprised of a slip ring assembly.

5. The apparatus according to claim 3 wherein said electrodes extend in parallel across said roller.

6. The apparatus according to claim 3 wherein said amlifying means compares the amplitude of the received voltage pulse against a transmitted voltage pulse to determine the conductivity of said conductive sheet.

* * * * *